(12) United States Patent
Muller

(10) Patent No.: US 7,720,191 B2
(45) Date of Patent: May 18, 2010

(54) COMPUTER TOMOGRAPHY APPARATUS

(75) Inventor: Timo Muller, Espoo (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 11/911,050

(22) PCT Filed: Apr. 11, 2006

(86) PCT No.: PCT/FI2006/050139

§ 371 (c)(1), (2), (4) Date: Oct. 9, 2007

(87) PCT Pub. No.: WO2006/108920

PCT Pub. Date: Oct. 19, 2006

(65) Prior Publication Data

US 2008/0165923 A1    Jul. 10, 2008

(30) Foreign Application Priority Data

Apr. 11, 2005   (FI)   ................... 20050365

(51) Int. Cl.
*A61B 6/14* (2006.01)
(52) U.S. Cl. ............ 378/38; 378/197; 378/20
(58) Field of Classification Search ............ 378/38–40, 378/193–197, 20, 208, 209
See application file for complete search history.

(56) References Cited

U.S. PATENT DOCUMENTS

| | | | |
|---|---|---|---|
| 5,058,147 A | 10/1991 | Nishikawa et al. | |
| 5,751,781 A | 5/1998 | Brown et al. | |
| 6,118,842 A | 9/2000 | Arai et al. | |
| 6,256,528 B1 | 7/2001 | Zonneveld et al. | |
| 6,456,684 B1 | 9/2002 | Mun et al. | |
| 6,466,641 B1 * | 10/2002 | Virta et al. | ............ 378/38 |
| 2003/0001056 A1 | 1/2003 | Ihalainen et al. | |
| 2004/0190678 A1 * | 9/2004 | Rotondo et al. | ............ 378/38 |

FOREIGN PATENT DOCUMENTS

| | | |
|---|---|---|
| DE | 19938955 A1 | 8/1999 |
| EP | 1457155 A1 | 9/2004 |
| JP | 06047040 | 2/1994 |
| WO | 03084407 A1 | 10/2003 |

OTHER PUBLICATIONS

Search Report, WOX.
Search Report, FIX.
Jian Hsich, "Computer Tomography: Principals, Design, Artifacts and Recent Advantages" 2003, SPIE Press, Belligham, Washington, US (WO 03/84407).

* cited by examiner

*Primary Examiner*—Courtney Thomas
(74) *Attorney, Agent, or Firm*—Cozen O'Connor

(57) ABSTRACT

This invention relates to a computer tomography apparatus, especially to a computer tomography apparatus intended for use in connection with odontological diagnostics. In the computer tomography apparatus according to the invention, it is essential that one has arranged thereto, in addition to a computer tomography imaging station, a second imaging station comprising second patient support means 16' at a distance from said computer tomography imaging station. The invention enables more versatile odontological imaging than prior art apparatuses, whereby one does not have to acquire to the clinic, in addition to the computer tomography apparatus, e.g. a separate skull-imaging device.

14 Claims, 3 Drawing Sheets

COMPUTER TOMOGRAPHY APPARATUS

Figure 1:
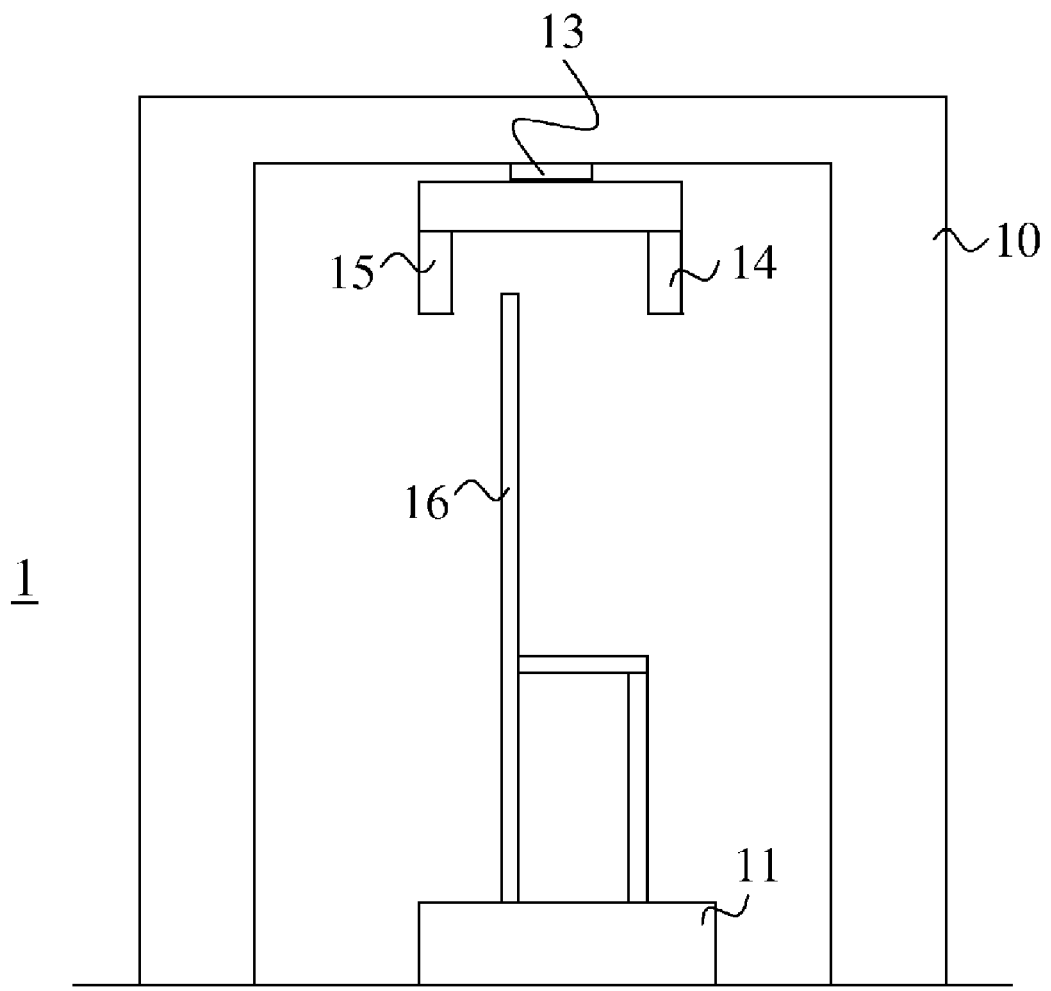

This invention relates to a computer tomography apparatus according to the preamble of claim 1, especially to a computer tomography apparatus intended for use in connection with odontological diagnostics.

Medical X-ray imaging has a long history. The earliest techniques were based on transillumination of the object to be imaged. In transillumination, all the anatomies of the volume being imaged possibly overlapping in the direction of radiation are imaged on the film on top of each other. In order to solve this problem, layer i.e. so-called tomographic imaging was later developed, by means of which it is possible to get the desired layer of the object to become imaged more clearly by causing blurring of the other layers of the object in the image being formed or in the image to be formed. Blurring is accomplished by changing the respective position of the imaging means and the object during an imaging event, depending on the imaging procedure, either during irradiation or between individual irradiations.

Later on, and especially along with the advancement of computers and digital imaging, a great number of different tomographic imaging techniques and devices have been developed. In the field of odontology one generally uses, in addition to intra-oral and cephalometric imaging, which are simpler as far as imaging-technology is concerned and are realised by transillumination imaging, among other things, so-called panoramic imaging in which, typically, a layer comprising the whole dental arch is imaged on a plane.

In conventional film-based panoramic imaging one scans across the dental arch by a narrow beam so that the centre of rotation of a turnable arm part, substantially to the opposite ends of which the imaging means have been positioned, is transferred linearly while the arm part is turned and at the same time the film, which is moving together with the arm part, is transferred through a narrow beam produced by the radiation source at a rate fulfilling the imaging condition of the imaging procedure in question. In digital panoramic imaging, the frequency by which the image data is read from the sensor during an imaging scan corresponds this transfer velocity of the film.

A conventional odontological cephalometric image is thus a transillumination image, which has been taken by using so large a beam and a film that one has been able to image the desired area at a go. Here one has applied so-called long-distance imaging technology, in which patient positioning with respect to the radiation source is realised by arranging the distance of the patient from the radiation source adequately long, in order that the image to be formed would not become distorted as a consequence of front and back portions of the skull being, relatively, at significantly different distances from the radiation source in the direction of the beam. With the arrival of digital age also to cephalometric imaging, it has nevertheless been realised as a rule by scanning slot imaging, because the imaging sensors of the size corresponding to that of the cephalo film have still until now been extremely expensive.

Lately, an interest has begun to arise to apply computer (or computed) tomography (CT), used earlier mainly in hospital environment, also in the field of odontology. As such, one has not been able to transfer these massive and expensive CT apparatuses of hospital use to the dental environment, on account of their size but especially also on account of their price.

Imaging-technically, several different CT technologies are known today. In CT imaging, the volume to be imaged is irradiated from different directions and, from the data thus acquired, a desired two- or three-dimensional image is reconstructed afterwards. By this kind of technology one is also able, in principle, to reconstruct, among other things, a two-dimensional image of a skull, of part or even of the whole dental arch outspread on a plane. As far as principles of computer tomography and its different applications are concerned, a reference can be made to the literature on the art, such as to *Computed Tomography: Principles, Design, Artifacts and Recent Advantages*, Jian Hsieh, SPIE PRESS, 2003, Bellingham, Wash., USA.

Medical computer tomography apparatuses conventionally comprise a horizontal plane on which the patient is positioned for the duration of imaging. Such devices are quite massive and expensive when comparing them e.g. to dental panoramic imaging devices. The great size and weight of CT devices has been a consequence of different limiting conditions of the imaging technology, such as the radiation intensity required. Because of the massive structure, one has tried to realise the relative movements of the imaging means and the object so that the imaging means themselves are arranged either stationary or to be turnable with respect to a stationary centre of rotation only, whereby the other possible movements may be realised by arranging the object to be imaged itself as movable.

A form of computer tomography is the so-called cone beam CT (CBCT) wherein one uses, as a distinction from the narrow beam used in e.g. panoramic imaging, a cone-like beam substantially the size of the dimensions of the volume to be imaged and, instead of a slot sensor, a detector the size of which corresponds the size of the beam in question. Compared to many of the more conventional CT imaging technologies, by the CBCT technology one is able to achieve significantly smaller radiation doses and shorter imaging times.

Lately, one has begun developing CT apparatuses intended especially for dental imaging. One such a CT device according to prior art has been presented in WO publication 03/84407. The body of the device in question forms a stabile gate-like structure under which a chair is arranged, into which the patient is positioned for the duration of imaging, as immovable as possible. The imaging means are arranged turnable on a plane around a centre of rotation, which is located as fixed with respect to the body part of the device. The chair functioning as a patient support is arranged movable in the x,y,z coordinate system, whereby the location of the centre of rotation of the imaging means, and the height position of the imaging means with respect to the anatomy of the patient, may be changed, if desired.

As is evident from what is presented above, there are several different imaging technologies that relate to dental X-ray imaging. Although CT apparatuses enable in principle reconstruction of a number of various kind of images, a problem concerning their use is, nevertheless, that in order to get image information for reconstruction, one has to expose the object to be imaged to significant radiation doses. Thus, in odontological X-ray imaging, one is easily faced with the ethical problem if exposing the patient to the radiation dose in question is justifiable with respect to the benefit potentially achievable from the imaging. Such a situation may also come across in a situation when the care process has reached a certain stage where it would be necessary to re-image the patient because of some particular single purpose, for which purpose CT imaging as such would be applicable but would be questionable considering the radiation stress to the patient—especially in case some other applicable X-ray imaging technique for this single purpose as such would exist, which would produce a smaller radiation dose. For example, a conventional cephalometric imaging exposes patient to a considerably smaller radiation stress than computer tomography imaging, whereby e.g. in connection with an orthodontic treatment, one may be faced with a problematic situation of the kind described above, whereupon at a dental clinic having invested in e.g. a single odontological CT imaging apparatus, one has to decide if a new CT image of the patient were to be taken in spite of all, if the patient were to be sent to be imaged elsewhere or if the imaging need in question is so recurring that it is justifiable to invest in another X-ray apparatus enabling the imaging in question.

On the other hand and additionally, considering e.g. producing volume information of the volume of the whole skull for reconstructing a conventional dental cephalometric image of the information produced by a CT device, one would have to use either quite a large-sized sensor or, alternatively, several irradiations for producing information from smaller partial volumes of the skull, before one would be able to reconstruct an image corresponding such a conventional cephalometric image of the information produced by a CT device. In this kind of reconstruction calculation, one would also have to still separately consider the fact that, during the imaging, the mutual distances between the radiation source, imaging sensor and the patient have been other than in conventional cephalometric imaging.

In spite of their principled versatility, the use of CT apparatuses according to prior art in dental environment thus, nevertheless, involves different practical problems, because one is not always and in all practical situations able to use them for producing all kinds of X-ray images typically required at a clinic, anyhow. The goal of the invention is thus to offer an X-ray imaging apparatus which diversifies the possibilities to use a customary CT apparatus especially for odontological X-ray imaging. A goal of the invention is especially an apparatus which also enables, besides CT imaging, at least so-called long-distance imaging, whereby e.g. the transillumination imaging of the skull may be realised with a radiation dose corresponding the patient dose of conventional cephalometric imaging. Although such an additional characteristic naturally always increases the acquisition costs of the device, it is nevertheless more cost-effective for the dental clinic to purchase a computer tomography device according to the invention than always purchase separate devices solely for each unique imaging need. The invention with its preferable embodiments significantly diversifies the possible uses of a computer tomography apparatus at a dental clinic.

The essential aspects of the invention and its preferable embodiments are presented in the characterising parts of the following claims. A computer tomography apparatus according to the invention comprises a construction which includes, in addition to a computer tomography imaging station, a second imaging station comprising second patient support means at a distance from said computer tomography imaging station, which distance is preferably at least 50 cm. Preferably, the imaging stations according to the invention are arranged to be located with respect to the radiation source of the apparatus, for the part of the tomography imaging station, at a distance substantially less than 150 cm, such as less than 130 cm, for example 20-80 cm, and, for the part of said second imaging station, at a distance of over 150 cm, such as of the order of 160-190 cm, preferably around 170 cm. Thus, arranging of a second imaging station in the apparatus does not disturb practical work in connection with computer tomography imaging, including patient positioning, and on the other hand, the apparatus will not become unnecessarily large in size, but the distance of the second imaging station from the radiation source is nevertheless adequate e.g. considering the requirements of long-distance X-ray imaging.

The present invention enables more versatile odontological imaging compared to CT imaging devices according to prior art, whereby there is no need to purchase e.g. a separate cephalometric imaging device to the clinic. With a device according to the invention, it is possible, in principle, to produce e.g. all X-ray images typically required in connection with orthodontic treatment by one and the same X-ray imaging apparatus, and considering enabling e.g. cephalometric imaging, there is no need for either purchasing a large-sized and thus extremely expensive area sensor, or for first producing information depicting more than one partial volume, only of which it would be possible to reconstruct a cephalometric image.

Figure 2:
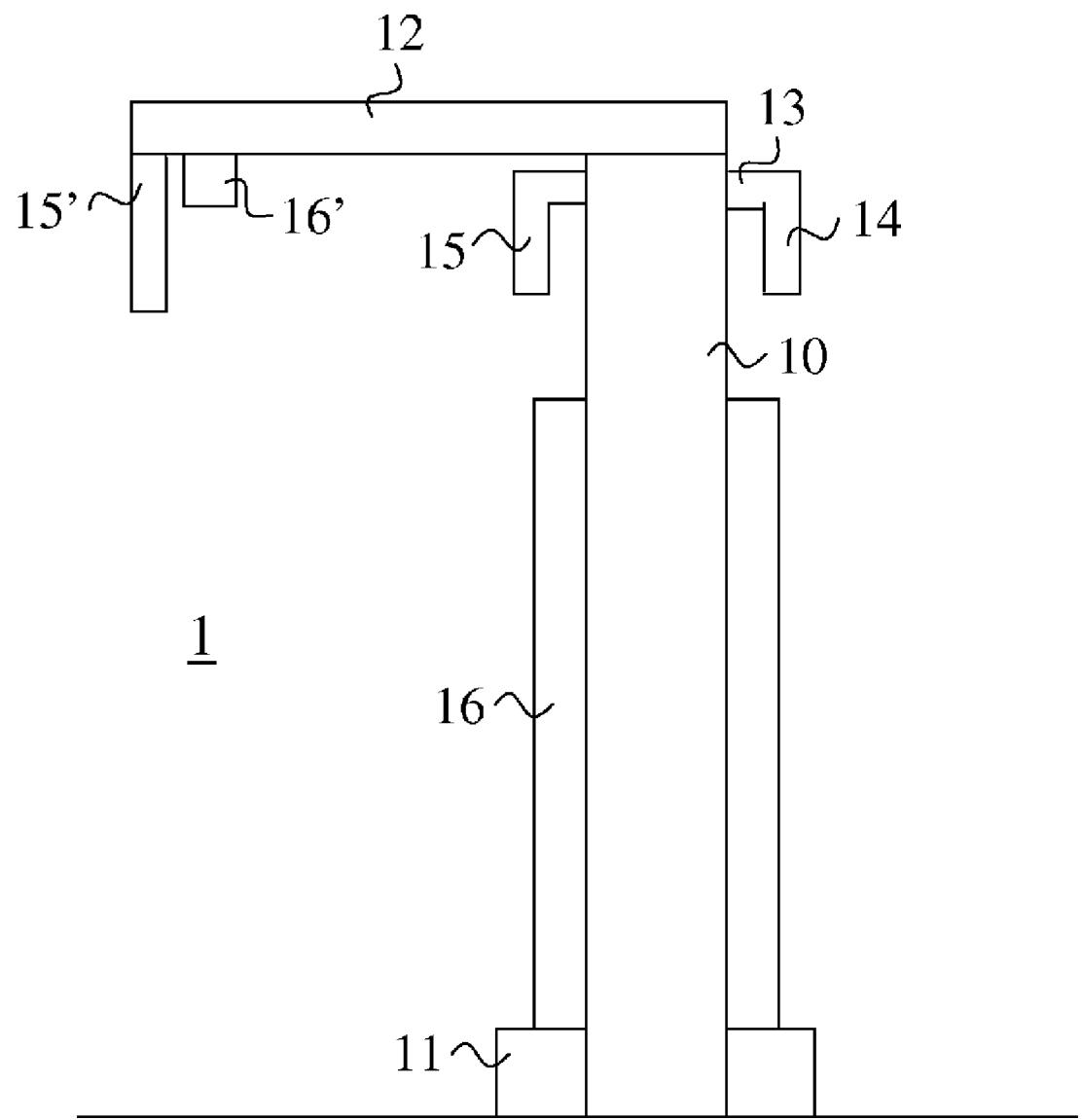
Figure 3:
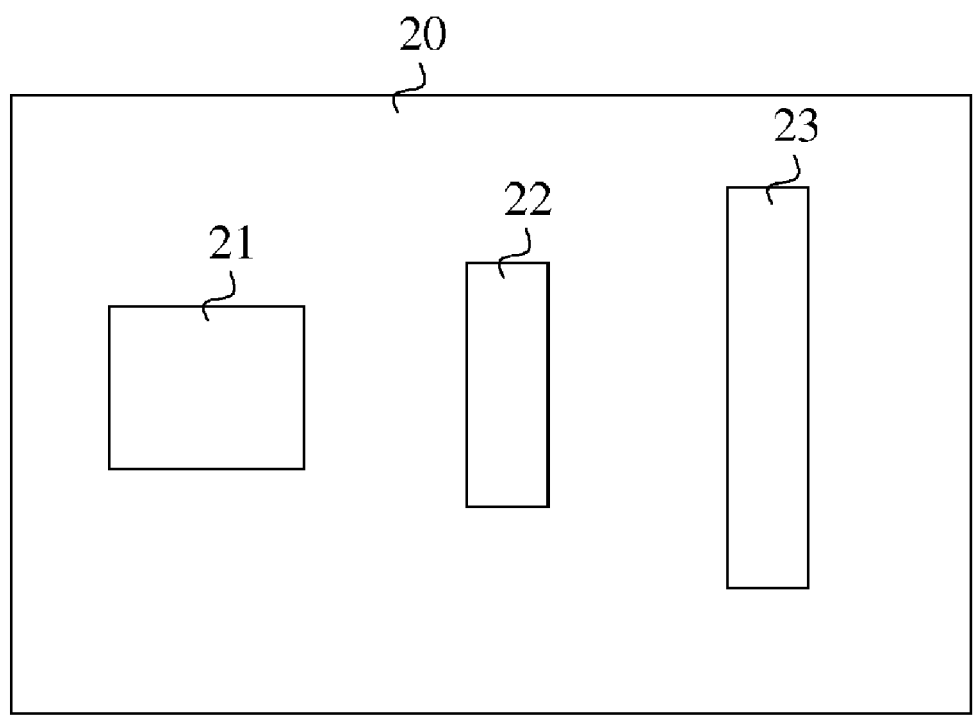

Some of the preferable embodiments and advantages of the invention will next be described also with reference to the accompanying figures, of which FIG. 1 presents a basic structure of a CT apparatus according to prior art, FIG. 2 presents a side view of the CT apparatus according to FIG. 1, provided with a second patient support station according to a preferable embodiment of the invention, and FIG. 3 presents a collimator plate applicable for use in a preferable embodiment of the invention.

A CT apparatus according to prior art of FIG. 1 comprises a gate-like support structure 10, in connection with which a construction 13 for moving imaging means 14, 15 (a radiation source 14 and an imaging sensor 15) may be arranged. Patient support means 16 included in the computer tomography imaging station of the apparatus comprise a chair, in connection with which means for positioning the head of the patient as immovable, not shown in detail in the figure, are arranged. The patient support means 16 may be arranged movable in the area of the patient support station by means of moving means 11, for positioning the patient to a desired position with respect to the imaging means 14, 15, and/or for moving during imaging. In connection with the radiation source 14, a collimator structure not shown in the figure is arranged, for limiting the radiation produced by the radiation source 14 to a beam. The apparatus includes a control system, which comprises control means and actuators for realising operation of the radiation source 14 and the imaging sensor 15 as well as for realising and controlling movements of them and/or of the patient support means 16.

FIG. 2 presents a side view of the CT apparatus according to FIG. 1, but as the imaging means being turned 90 degrees from the position of FIG. 1. A second imaging station comprising second patient support means 16' is arranged to the apparatus, in the solution according to FIG. 1, arranged to the stationary arm 12 which is connected to the support structure 10. Substantially to the end of the arm 12, to the substantial vicinity of the other patient support means 16', is arranged also a second imaging sensor 15'. The second imaging station is thus located at a distance, such as at least 50 cm, farther from the radiation source 14 than the computer tomography imaging station 16. Naturally, the arm 12 does not have to be arranged, with respect to the support structure 10 of the apparatus 1, particularly in the direction shown in FIG. 2, nor the arm 12 to be exactly similar to that shown in FIG. 2.

As one may arrange the imaging means of the CT apparatus movable with respect to the tomography imaging station, or vice versa, talking about the aforementioned 50 cm distance as such is not necessarily unambiguously accurate. It is obvious, though, that in context of this invention, one means a distance in a situation where the imaging means are positioned for imaging and/or where they move during imaging.

Taking this into consideration, one may thus note that the computer tomography imaging station is preferably arranged to be located substantially between the imaging means at a distance of the order of 20-80 cm from the radiation source and, correspondingly, the second imaging station according to the invention at a distance of at least of the order of 130 cm, such as around 170 cm, from the radiation source, when the apparatus is positioned for imaging to be realised in this second imaging station.

The basic structure of the CT apparatus according to the invention may also be of another kind than that shown in FIG. 1. The apparatus may preferably comprise e.g. a column-like support structure 10, in association with which a tomography imaging station comprising a patient support means 16 has been arranged, and wherein the imaging means 14, 15 have been arranged to a construction 13 diverging from the support structure and consisting of possibly more than one arm part, the construction being arranged to move the imaging means 14, 15 with respect to said tomography imaging station. Especially in connection with such a preferable embodiment of the invention, the construction 13 comprising the imaging means of the apparatus may comprise an arm part comprising imaging means 14, 15, which arm part is connected to said support structure 10 of the apparatus or to some other, with respect to the aforementioned first patient support 16 fixed structure, via at least two other turnable arm parts, which each at least two arm parts have been arranged turnable with respect to two centres of rotation locating at a distance from each other, substantially on the same plane, out of which centres of rotation the outmost centres of rotation of the outmost arm parts of said at least two arm parts connect, first, to said arm part comprising imaging means and, second, to said support structure 10 or other structure being fixed with respect to said first patient support means 16. Especially in such an embodiment of the invention, the imaging means 14, 15 are preferably arranged, to an arm part 13 comprising the imaging means, at a distance of the order of 50 cm from each other.

It was mentioned above that the apparatus according to FIG. 2 includes a second imaging sensor 15' arranged in connection with the second imaging station. In this second imaging station one may use as an alternative film, too, in which case one must understand the reference number 15' referring to means for attaching a film cassette. It is further possible, in principle, to use the same imaging sensor 15 in both of the imaging stations, in which case one may interpret the reference number 15' meaning a sensor holder for releasable connection of the imaging sensor 15. In that case, naturally, also in connection with the computer tomography imaging station, such a sensor holder is arranged which enables releasable connection of the imaging sensor 15.

The second imaging station according to the invention may favourably be used for odontological cephalometric imaging. Then, at least in connection with this second imaging station, such an imaging sensor 15, 15' is preferably used whose at least one dimension has been arranged to substantially correspond the corresponding dimension of patient's skull or, correspondingly, the dimensions of the film cassette comprising film, arranged to be attached to this imaging station, have been arranged to substantially correspond the dimensions of patient's skull. If the same imaging sensor 15 is used in both imaging stations, both its dimensions and the detector itself have to be arranged to enable use of the imaging sensor 15 for both computer tomography imaging, preferably especially for cone-beam computer tomography imaging, and for transillumination imaging of patient's skull—or for an electric scanning imaging at least substantially corresponding it.

The usability of the CT apparatus according to the invention may be extended further by realising its control system, the construction for moving imaging means and the computer tomography imaging station, together with means included therein, such that, in the computer tomography imaging station, one may also take a conventional dental panoramic or other layer image which is based on blurring of desired image information. In that case, as in FIG. 3, a collimator 20 locating in association with the radiation source can be arranged to comprise e.g. at least three different openings, one of which being arranged as substantially square-shaped 21, to be used in connection with cone-beam CT to be realised at the computer tomography imaging station, one as slot-like 23, to be used in connection with scanning slot imaging to be realised at said second imaging station, and at least one as slot-like but as lower than the abovementioned one 22, to be used in connection with said panoramic or other imaging being based on blurring of image information. If one wishes to realise the scanning slot imaging at the second imaging station according to the invention by keeping the radiation source stationary, the collimator plate 20 has to be arranged movable. On the other hand, the collimator structure may be realised so that at least one opening being adjustable in size, e.g. in one dimension, has been arranged to it, or e.g. so that only one opening, being adjustable in at least two dimensions, has been arranged to it.

The second imaging station according to the invention does not necessarily have to be a second imaging station physically, but it may also be realised virtually either so that the position of at least either the radiation source, or the structures forming the computer tomography imaging station itself, has been arranged movable. Then, said first patient support means 16 may be arranged either to be applicable for use in both imaging stations, i.e. in both imaging techniques realised by the apparatus, or in connection therewith a second patient support means 16' has been arranged, which are used also in this second imaging. The idea according to the invention will also be realised by arranging a second radiation source to the apparatus, in such a way that it will locate at a different distance from the computer tomography imaging station than the first radiation source.

It is favourable to realize the present invention so that the patient can be positioned to be immovable, at least on a horizontal plane, to the body of the apparatus or to another stationary patient station, and the movements required to change the relative position of the patient and the imaging means are realised by moving the imaging means.

Especially and preferably, the imaging means of the CT apparatus according to the invention include an area sensor, a so-called Frame Sensor, used in CBCT imaging. The active surface of the detector may be circular, or a rectangle whose dimensions are preferably substantially of the same order of magnitude, such as e.g. at least 10×10 cm, such as 12×12 cm, or e.g. 20×20 cm, or a detector having a corresponding diameter. By arranging collimation of the beam produced by the radiation source to correspond dimensions of such a detector, and by using a source-image distance (SID) of the order of e.g. 50 cm, it is possible to realise the radiation source of the apparatus according to the invention as considerably lighter than those of conventional computer tomography devices. Thus, also the arm structure may be realised as relatively light, e.g. as described above as an example not shown in the figures, as a structure comprising more than one arm part. With the advancement of sensor technology, it should also be economically possible to use such a large sensor in the apparatus according to the invention that it will be applicable for use in both imaging stations of the apparatus.

It is also possible to realise the invention according to an embodiment not shown in the figures so that a freedom of movement in vertical direction is arranged to the construction 13 comprising the imaging means 14, 15, too. For example, in an apparatus including a vertical column-like support structure 10, this may be realised, among other thins, so that the patient support means 16 is made to move along the vertical movement of the structure 13 comprising the imaging means 14, 15, or by arranging an independent freedom of vertical movement to it, and to the construction 13 comprising the imaging means. Then, positioning of the location of the volume to be imaged will be possible also in vertical direction without moving the patient.

It is obvious to a man skilled in the art that, especially along with advancement of technology, the basic idea of the invention may be realised in many different ways and its different embodiments are not limited to the examples described above, but they may vary within the scope of the inventive idea according to the application and the scope as defined in the accompanying claims.

The invention claimed is:

1. A computer tomography apparatus, which includes:
a computer tomography imaging station for taking CT scans including imaging means, said computer tomography imaging station having a construction for rotating said imaging means (14, 15) being connected to a support structure 10, which imaging means comprise a radiation source (14) and an imaging detector (15), and wherein said construction is structured and arranged to enable rotating said radiation source and imaging detector about a fixed axis of rotation; a collimator structure (20) arranged for limiting radiation produced by the radiation source (14) to a beam of at least one shape, a first patient support means (16) arranged in connection with the apparatus, and a control system which includes control means and actuators to realize operation of the radiation source (14), the imaging detector (15), and the patient support means, (16), and
wherein said computer tomography apparatus further includes a second imaging station arranged at a distance from said computer tomography imaging station and including a second patient support means (16').

2. An apparatus according to claim 1, wherein said imaging stations are arranged to be located so that the second imaging station is located at a distance farther from the radiation source (14) than said computer tomography imaging station, when the imaging means (14, 15) are positioned for imaging.

3. An apparatus according to claim 2, wherein said distance is around 50 cm, at least.

4. An apparatus according to claim 1, wherein said computer tomography imaging station is arranged to be located substantially between the imaging means (14, 15), at a distance of the order of 20-80 cm from the radiation source (14), when the imaging means of the apparatus are located in their imaging positions and/or are moving during computer tomography imaging, and, correspondingly, said second imaging station at a distance of at least of the order of 130 cm, such as around 170 cm, from the radiation source (14), when the apparatus is positioned for imaging to be realized in this second imaging station.

5. An apparatus according to claim 1, wherein association with said second imaging station, in the substantial vicinity of said second patient support means (16'), either a second imaging sensor (15') or a means for detachable connection of the imaging sensor (15, 15') or a film cassette is arranged.

6. An apparatus according to claim 1, wherein at least in said second imaging station, an imaging detector (15, 15') is used at least one dimension of which is arranged to substantially correspond the corresponding dimension of patient's skull or, correspondingly, the dimensions of the film cassette arranged to be connected thereto are arranged to substantially correspond the dimensions of patient's skull.

7. An apparatus according to claim 1, wherein said control system, construction (13) for moving the imaging means (14, 15) and said computer tomography imaging station, with the means included therein, of the apparatus are realized such that, at the computer tomography imaging station, one is also able to realize a conventional odontological panoramic or other imaging being based on blurring of image information.

8. An apparatus according to claim 1, wherein a movable collimator plate (20) is arranged in connection with the radiation source, which collimator plate comprises at least three different openings, one of which is arranged to be used in connection with cone beam tomography imaging to be realized at the computer tomography imaging station, one to be used in connection with scanning slot imaging realized in said second imaging station, and at least one to be used in connection with said panoramic or other imaging being based on blurring of image information.

9. An apparatus according to claim 1, wherein the dimensions of said imaging detector (15) used at the computer tomography imaging station and the technology of the detector itself, as well as the technology being in association therewith, are arranged to enable use of the imaging detector (15) in question for both computer tomography imaging, especially for cone-beam computer tomography imaging, and for transillumination or substantially corresponding electric imaging of the patient's skull to be realized by scanning technique.

10. An apparatus according to claim 9, wherein the imaging detector (15) in question is arranged to the apparatus as releasably connected, on one hand, to a sensor holder arranged in connection with the computer tomography imaging station, on the other hand, at least to a sensor holder arranged in connection with at least said second imaging station.

11. An apparatus according to claim 1, wherein said second imaging station is arranged to be formed virtually either so that at least either the radiation source (14) or said computer tomography imaging station is arranged movable, in which case said first patient support means (16) is arranged either to be applicable for use in both imaging stations, or the second patient support means (16'), to be used also at the second imaging station (16'), is arranged in connection with it, or so that also a second radiation source is arranged to the apparatus, at a different distance from said computer tomography imaging station.

12. An apparatus according to claim 1, wherein said construction (13) comprising the imaging means (14, 15) comprises an arm part, which is connected to said support structure (10), or some other structure of the apparatus which is fixed with respect to the aforementioned first patient support means (16), via at least two other turnable arm parts, which each at least two arm parts are arranged turnable with respect to two centres of rotation locating at a distance from each other substantially on the same plane, out of which centres of rotation, the farthest centres of rotation of the farthest arm parts of said at least two arm parts connect to, on one hand, to said arm part comprising imaging means and, on the other hand, to said support structure (10) or other structure which is fixed with respect to said first patient support means (16).

13. An apparatus according to claim 12, wherein said imaging means (14, 15) are arranged to said arm part (13) comprising the imaging means at a distance of the order of 50 cm from each other.

14. An apparatus according to claim 1, wherein said construction for moving imaging means and said control system of the apparatus are arranged to enable moving of the imaging means so that they follow a trajectory enabling dental panoramic imaging.

* * * * *